(12) United States Patent
Hartman et al.

(10) Patent No.: US 6,509,167 B1
(45) Date of Patent: Jan. 21, 2003

(54) HIGH THROUGHPUT SARCOMERIC ASSAY

(75) Inventors: James J. Hartman, San Francisco, CA (US); Fady Malik, Burlingame, CA (US); Roman Sakowicz, Foster City, CA (US); Jeffrey T. Finer, Foster City, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 33 days.

(21) Appl. No.: 09/724,069

(22) Filed: Nov. 28, 2000

Related U.S. Application Data

(63) Continuation of application No. 09/539,164, filed on Mar. 29, 2000.

(51) Int. Cl.$^7$ ................................................. C12Q 1/44

(52) U.S. Cl. ............................ 435/19; 424/9.2; 435/21; 435/29

(58) Field of Search ............................. 435/19, 21, 29, 435/69.2; 424/9.1, 9.2

(56) References Cited

U.S. PATENT DOCUMENTS

| | | | | |
|---|---|---|---|---|
| 5,439,883 A | * | 8/1995 | Karsanov et al. | ............... 514/6 |
| 6,194,632 B1 | * | 2/2001 | Leiden | ........................ 800/3 |

FOREIGN PATENT DOCUMENTS

| | | | |
|---|---|---|---|
| WO | WO 01/02598 A2 | * | 1/2001 |

OTHER PUBLICATIONS

"Methods to Characterize Actin Filament Networks", Pollard, T.D. and Cooper, J.A., Methods Enzymol vol. 85 Pt B, 1982 pp 211–233.

"Methods to Measure Actin Polymerization", Cooper, J.A. and Pollard, T.D. Methods Enzymol vol. 85 Pt B, 1982 pp 182–210.

"The Rate Constant for ATP Hydrolysis by Polymerized Actin", Pollard, T.D and Weeds, A.G., FEBS Lett vol. 170 No. 1 May 7, 1984 pp 94–98.

"Assays for Myosin", Pollard, T. D., Methods Enzymol vol. 85 Pt B, 1982 pp. 123–130.

"Purification of Nonmuscle Myosins", Pollard, T. D., Methods Enzymol vol. 85 Pt B, 1982 pp. 331–356.

"Inhibition of acanthamoeba actomyosin–II ATPase activity and mechanochemical function by specific monoclonal antibodies", Kiehart, D. P.and Pollard, T. D., J Cell Biol vol. 99 No. 3, Sep. 1984 pp. 1024–1033.

"Transient kinetic analysis of rhodamine phalloidin binding to actin filaments", De La Cruz, E. and Pollard, T. D., Biochemistry vol. 33 No. 48,Dec. 6, 1994 pp. 14387–14392.

"Mechanical properties of actin filament networks depend on preparation, polymerization conditions, and storage of actin monomers.", Xu, J.; Schwarz, W.H.; Kas, J.A.; Stossel, T. P.; Janmey, P. A.; Pollard, T. D., Biophys J vol. 74, No. 5, May 1998 pp. 2731–2740.

"In vitro assays of processive myosin motors", Rock, R. S.; Rief, M.; Mehta, A. D.; Spudich, J. A., Methods vol. 22, Dec. 2000,pp. 373–381.

"The sequence of the myosin 50–20K loop affects Myosin's affinity for actin throughout the actin–myosin ATPase cycle and its maximum ATPase activity", Murphy, C. T.; Spudich, J. A., Biochemistry vol. 38 No. 12 Mar. 23, 1999 pp. 3785–3792.

"Specialized conservation of surface loops of myosin: evidence that loops are involved in determining functional characteristics", Goodson, H. V.; Warrick, H. M.; Spudich, J. A., J Mol Biol vol. 287 No. 1 Mar. 19, 1999 pp. 173–185.

"Kinetic characterization of myosin head fragments with long–lived myosin ATP states.", Friedman, A. L.; Geeves, M. A.; Manstein, D. J.; Spudich, J. A., Biochemistry vol. 37 No. 27 Jul. 7, 1998 pp. 9679–9687.

"Dictyostelium myosin 25–50K loop substitutions specifically affect ADP release rates", Murphy, C. T.; Spudich, J. A., Biochemistry vol. 37 No. 19, May 12, 1998, pp. 6738–6744.

"Phenotypically selected mutations in myosin's actin binding domain demonstrate intermolecular contacts important for motor function", Giese, K. C.; Spudich, J. A., Biochemistry vol. 36 No. 28, Jul. 15, 1997 pp. 8465–8473.

"Structure–function analysis of the motor domain of myosin", Ruppel, K. M.; Spudich, J.A., Annu Rev Cell Dev Biol, vol. 12, 1996 pp. 543–573.

"Characterization of single actin–myosin interactions", Finer, J. T.; Mehta, A. D.; Spudich, J. A., Biophys J, vol. 68, No. 4 Suppl Apr. 1995 , pp. 291S–296S.

"Enzymatic activities correlate with chimaeric substitutions at the actin–binding face of myosin", Uyeda, T. Q.; Ruppel, K. M.; Spudich, J. A., Nature ,vol. 368, No. 6471, Apr. 7, 1994 pp. 567–569.

"In vitro methods for measuring force and velocity of the actin–myosin interaction using purified proteins", Warrick, H. M.; Simmons, R. M.; Finer, J. T.; Uyeda, T. Q.; Chu, S.; Spudich, J. A., Methods Cell Biol, vol. 39,1993, pp. 1–21.

"Assays for actin sliding movement over myosin–coated surfaces", Kron, D.J.; Toyoshima, Y. Y.; Uyeda, T. Q.; Spudich, J. A., Methods Enzymol. vol. 196, 1991 pp. 399–416.

(List continued on next page.)

Primary Examiner—Ralph Gitomer
(74) Attorney, Agent, or Firm—Beyer Weaver & Thomas, LLP

(57) ABSTRACT

The present invention provides high throughput screening systems for identifying compounds that modulate the biological activity of a biochemically functional sarcomere. The method can be performed in plurality simultaneously with fluorescence or absorbance readouts.

12 Claims, 3 Drawing Sheets

OTHER PUBLICATIONS

"The myosin step size: measurement of the unit displacement per ATP hydrolyzed in an in vitro assay", Toyoshima, Y. Y.; Kron, S. J.; Spudich, J. A., Proc Natl Acad Sci U S A vol. 87 No. 18 , Sep. 1990 pp. 7130–7134.

"Myosin subfragment–1 is sufficient to move actin filaments in vitro", Toyoshima, Y. Y.; Kron, S. J.; McNally, E. M.; Niebling, K. R.; Toyoshima, C.; Spudich, J. A., Nature vol. 328 No. 6130 Aug. 6–12 1987 pp. 536–539.

"Fluorescent actin filaments move on myosin fixed to a glass surface", Kron, S. J.; Spudich, J. A., Proc Natl Acad Sci U S A vol. 83 No. 17 Sep. 1986 pp. 6272–6276.

"Myosin movement in vitro: a quantitative assay using oriented actin cables from Nitella", Sheetz, M. P.; Block, S. M.; Spudich, J. A., Methods Enzymol vol. 134, 1986, pp. 531–544.

"Movement of myosin–coated beads on oriented filaments reconstituted from purified actin", Spudich, J. A.; Kron, S. J.; Sheetz, M. P., Nature, vol. 315 No. 6020 Jun. 13–19, 1985 pp. 584–586.

"ATP–dependent movement of myosin in vitro: characterization of a quantitative assay", Sheetz, M. P.; Chasan, R.; Spudich, J. A., J Cell Biol, vol. 99, No. 5 Nov. 1984 pp. 1867–1871.

"Purification of muscle actin", Pardee, J. D.; Spudich, J. A., Methods Enzymol vol. 85 Pt B 1982 pp. 164–181.

"Purification of muscle actin", Pardee, J. D.; Spudich, J. A., Methods Cell Biol vol. 24 1982 pp. 271–289.

US Patent application No. 09/314,464, Finer et al., Filed May 18, 1999, Title: Compositions And Assays Utilizing ADP Or Phosphate For Detecting Protein Modulators.

Sanger J. Use of Fluorescent Probes to Study Myofibrillogenesis. Cellular and Molecular Biology 93:221–235, 1988.*

Brenner B. Thin Filament Activation Probed by Fluorescence . . . Biophysical Journal 77(5)2677–91, Nov. 1999.*

* cited by examiner

Compound 1

Compound 2

HIGH THROUGHPUT SARCOMERIC ASSAY

This Application is a continuation of application Ser. No. 09/539,164 filed Nov. 29, 2000.

FIELD OF THE INVENTION

The invention relates to methods for the identification of contractile modulators of the cardiac sarcomere and use of such methods for the identification of therapeutic agents.

BACKGROUND OF THE INVENTION

Congestive heart failure is a growing epidemic in our aging population. Its prevalence has been growing as the population ages and as cardiologists are more successful at reducing mortality from ischemic heart disease, the most common cause of congestive heart failure. Roughly 4.6 million people in the United States have heart failure with an incidence approaching 10 per 1000 after age 65 years. Hospital discharges for congestive heart failure rose from 377,000 in 1979 to 957,000 in 1997 making congestive heart failure the most common discharge diagnosis in people age 65 and over. The five year mortality from congestive heart failure approaches 50%. Hospitalization for heart failure is usually the result of inadequate outpatient therapy. Hence, while heart failure therapy has greatly improved over the last several years, new and better therapies are still required to improve these still dismal statistics.

Inotropes are drugs that increase the contractile ability of the heart. As a group, all current inotropes have failed to meet the gold standard for heart failure therapy, that is, to prolong patient survival (FDA Cardiorenal Panel: Minutes Jan. 27, 1998 afternoon session, www fda.gov). Despite this fact, intravenous inotropes continue to be widely used in acute heart failure to allow for reinstitution of oral medications or to bridge patients to heart transplantation, whereas in chronic heart failure, oral digoxin is used as an effective inotrope to relieve patient symptoms, improve the quality of life, and reduce hospital admissions for heart failure.

Currently, there is a paucity of agents that can safely improve cardiac function; most agents have detrimental side effects if given for more than a few days. As for chronic inotropic use, only digoxin has proven safe to administer even though it has a narrow therapeutic range. The most recently approved short-term intravenous agent, milrinone, is now over ten years old. The only available oral drug, digoxin, is over 200 hundred years old. There is a great need for agents that exploit new mechanisms of action and may have better outcomes in terms of relief of symptoms, safety, and patient mortality, both short-term and long-term. The present invention provides methods for identifying such agents.

SUMMARY OF THE INVENTION

The present invention provides methods to identify candidate agents that bind to a protein or act as a modulator of the binding characteristics or biological activity of a protein. In one embodiment, the method is performed in plurality simultaneously. For example, the method can be performed at the same time on multiple assay mixtures in a multi-well screening plate. Furthermore, in a preferred embodiment, fluorescence or absorbance readouts are utilized to determine activity. Thus, in one aspect, the invention provides a high throughput screening system.

In one embodiment, the present invention provides a method of identifying a candidate agent as a modulator of the activity of a target protein complex. Preferably, the target protein complex either directly or indirectly produces ADP or phosphate. More preferably, the target protein complex comprises a preparation comprising one or more of the following proteins: myosin, actin, and cardiac regulatory proteins. In a particularly preferred embodiment, the target protein complex is a reconstituted sarcomere consisting of actin, myosin, and the cardiac regulatory proteins.

The method further comprises adding a candidate agent to a mixture comprising the target protein complex under conditions that normally allow the production of ADP or phosphate. The method further comprises subjecting the mixture to an enzymatic reaction that uses said ADP or phosphate as a substrate under conditions that normally allow the ADP or phosphate to be utilized and determining the level of activity of the enzymatic reaction as a measure of the concentration of ADP or phosphate. The phrase "use ADP or phosphate" means that the ADP or phosphate are directly acted upon. In one case, the ADP, for example, can be hydrolyzed or can be phosphorylated. As another example, the phosphate can be added to another compound. As used herein, in each of these cases, ADP or phosphate is acting as a substrate. A change in the level between the presence and absence of the candidate agent indicates a modulator of the target protein complex.

DETAILED DESCRIPTION OF THE INVENTION

I. Definitions

Figure 1:
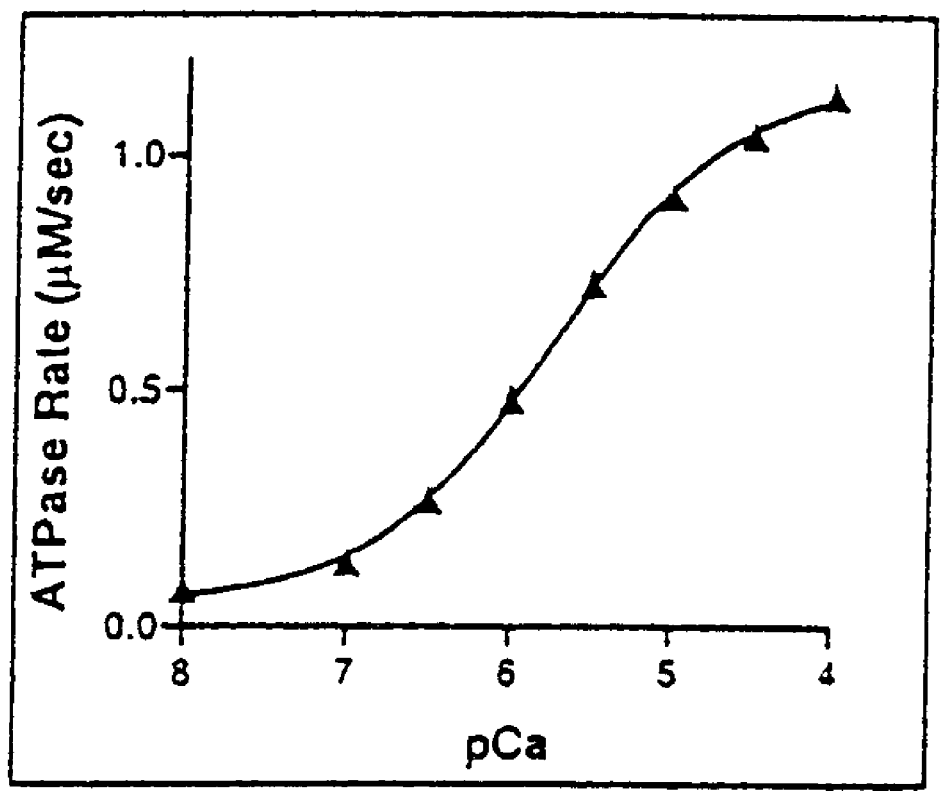
FIG. 1 graphically demonstrates that the ATPase rate of the reconstituted system responds in a calcium dependent manner. The conditions used are S1 at 1.25 $\mu$m, actin at 14 $\mu$m Tn complex consisting of TnC, TnI, and TnT at 3 $\mu$m and Tm at 2 $\mu$m in a buffer containing 12 mM K-Pipes pH 6.8, 2 mM $MgCl_2$, 1 mM ATP, 1 mM DTT, and 0.1 mg/ml BSA. The y-axis represents the rate of ATP hydrolysis.

"Target protein complex" refers to a protein or combination of proteins that directly or indirectly produces ADP or phosphate. A particularly preferred target protein complex is a biochemically functional sarcomere preparation comprising myosin, actin, tropomyosin, and the troponin complex. As such, preferred target proteins include, but are not limited to, cytoskeletal proteins including, but not limited to, myosins, actins, tropomyosins, and troponins. Suitable target proteins also include fragments of these proteins. In a preferred embodiment, one or more of the target proteins is derived from mammalian cells.

The terms "isolated", "purified", or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography.

The terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

"Candidate agent" (used interchangeably herein with "test composition" and "test compound" and "test agent") refers to a molecule or composition whose effect on the target proteins is desired to assay. The "candidate agent" can be any molecule or mixture of molecules, optionally in a suitable carrier.

By "ATPase" herein is meant an enzyme that hydrolyzes ATP. ATPases include proteins comprising molecular motors such as myosins.

A "therapeutic" as used herein refers to a compound that is believed to be capable of modulating the contractility of the cardiac sarcomere in vivo that can have application in both human and animal disease. Modulation would be desirable in a number of conditions including, but not limited to, congestive heart failure and diastolic heart failure.

II. The Target Protein Complex

A. Overview of the Sarcomere

Comprising nearly 60% of cardiac cell volume is the cardiac sarcomere. The sarcomere is an elegantly organized cellular structure found in cardiac and skeletal muscle made up of interdigitating thin and thick filaments. The thick filaments are composed of myosin, the protein responsible for transducing the chemical energy of ATP hydrolysis to force and directed movement. Myosin and its functionally related cousins are called motor proteins. The thin filaments are composed of a complex of proteins. Actin is a filamentous polymer and is the substrate upon which myosin pulls during force generation. Bound to actin are a set of regulatory proteins, the troponin complex and tropomyosin, that make the actin-myosin interaction dependent on changes in intracellular $Ca^{2+}$ levels. With each heart beat, $Ca^{2+}$ levels rise and fall, initiating cardiac muscle contraction and then cardiac muscle relaxation (Robbins J and Leinwand L A. (1999) *Molecular Basis of Cardiovascular Disease*, Chapter 8. editor Chien, K. R., W. B. Saunders, Phil. Each of the components of the sarcomere contributes to its contractile response.

B. Myosin

The most extensively studied of all the motor proteins is myosin. Of the thirteen distinct classes of myosin in human cells, myosin-II is the form responsible for contraction of skeletal, cardiac, and smooth muscle. This form of myosin is significantly different in amino acid composition and in overall structure from myosins in the other twelve distinct classes (Goodson H V and Spudich J A. (1993) Proc. Natl. Acad. Sci. USA 90:659–663). Myosin-II consists of two globular head domains, called Subfragment-1 or S 1, linked together by a long β-helical coiled-coiled tail. Proteolysis of myosin generates either S-1 or heavy meromyosin (HMM, a two-headed form with a truncated tail), depending on conditions. S1 contains the ATPase and actin-binding properties of the molecule. S1 has been shown to be sufficient to move actin filaments in vitro (Toyoshima Y Y, Kron S J, McNally E M, Niebling K R, Toyoshima C, and Spudich J A. (1987) Nature 328:536–539), and is therefore clearly the motor domain of the molecule.

The high resolution crystal structure for skeletal S1 is known in both its putative pre-stroke and post-stroke states (Rayment I, Rypniewski W R, Schmidt-Base K, Smith R, Tomchick D R, Benning M M, Winkelmann D, Wesenberg G, Holden H M. (1993) Science 261:50–58 and Dominguez R, Freyzon Y, Trybus K M, Cohen C. (1998) Cell 94:559–571). S1 consists of a globular actin-binding and nucleotide-binding region known as the catalytic domain. This domain is attached at its carboxy-terminus to an α-helix that has two light chains of ~20 kDa each wrapped around it. This light-chain binding domain of S1 is known as the lever arm. Upon transitioning from the pre-stroke to the post-stroke state of the S1, the lever arm swings through an angle of ~90° about a fulcrum point in the catalytic domain near the nucleotide-binding site. The "power stroke" is driven by the hydrolysis of ATP.

The other end of the myosin molecule is an α-helical coiled-coiled tail involved in self assembly of myosin molecules into bipolar thick filaments. These thick filaments interdigitate between thinner actin filaments in the sarcomere, and the two filament systems slide past one another during contraction of the muscle. This filament sliding mechanism involves conformational changes in the myosin heads causing them to walk along the thin actin filaments at the expense of ATP hydrolysis.

Mammalian heart muscle consists of two forms of cardiac myosin, α and β, and they are well characterized (Robbins, supra). The beta form is the predominant form (>90 percent) in adult human cardiac muscle. Both have been observed to be regulated in human heart failure conditions at both transcriptional and translational levels (Miyata supra), with the alpha form being down-regulated in heart failure.

The sequences of all of the human skeletal, cardiac, and smooth muscle myosins have been determined. While the cardiac α and β myosins are very similar (93% identity), they are both considerably different from human smooth muscle (42% identity) and more closely related to skeletal myosins (80% identity).

Conveniently, cardiac muscle myosins are incredibly conserved across mammalian species. For example, both α and β cardiac myosins are >96% conserved between humans and rats, and the available 250-residue sequence of porcine cardiac β myosin is 100% conserved with the corresponding human cardiac β myosin sequence.

C. The Regulatory Proteins

The regulatory proteins are a set of four proteins that bind to the actin filament and confer calcium regulation. More specifically, they prevent myosin binding in the absence of calcium. Tropomyosin (Tm) is a long coiled-coiled alpha-helix that sits in the groove of the actin filament and sterically prevents myosin binding. The troponin complex is comprised of three proteins, troponin C, troponin I, and troponin T (TnC, TnI, and TnT, respectively), that confer calcium sensitivity to the actin filament.

TnC is the calcium sensor, containing four calcium binding sites. The crystal structure of its skeletal counterpart is solved (Houdusse A, Love M L, Dominguez R, Grabarek Z, Cohen C. (1997) Structure 5(12):1695–711). Two of the sites are exchangeable and become occupied as intracellular calcium increases at the initiation of cardiac contraction. Communicating via TnI and TnT, this calcium binding results in a movement of Tm out of the actin filament groove exposing binding sites for the myosin motors (Lehman W, Vibert P, Uman P, Craig R. (1995) J Mol Biol 251(2):191–6). Muscle contraction ensues. At the conclusion in the cardiac cycle, the process reverses and relaxation ensues.

The troponins are only found in skeletal and cardiac muscle while different tropomyosin genes are expressed in many cell types. The genomics of tropomyosin and the troponins are complicated by the fact that there are many splice variants of tropomyosin and TnT. However, again the general rule is that conservation of cardiac sequences is extremely high across different species (90% identity or more) while in the same species different tissues have more divergent sequences (<65% identity).

D. Actin

The complete sequences of the various actin isoforms have been established, and they all show >98% identity (Vandekerckhove & Weber 1979). Again, conservation across animal species is extremely high. Human cardiac $\alpha$ actin, for example, is 100% identical to its chicken counterpart. Unlike myosin though, human cardiac $\alpha$ actin only has four amino acid changes when compared to human skeletal muscle actin.

A further embodiment of this invention provides for a method for producing actin wherein actin is precipitated from a solution in the presence of high concentration of a magnesium salt, preferably magnesium chloride. Actin paracrystals which form under these conditions can be precipitated at significantly lower centrifugation speed than those used in conventional procedures for F-actin (for example, see J. D. Pardee and J. A. Spudich, Purification of muscle actin, Methods in Cell Biology, v. 24, pp.271–289, 1982). Additional advantage is that polymerization and wash are performed in a single step. Generally, a concentration of at least 10 mM is used. More preferably, the magnesium chloride will be present at a concentration of from about 25 to about 100 mM; more preferably, from about 40 to about 60 mM. In a preferred embodiment, a concentration of 50 mM was used.

E. A Biochemically Functional Sarcomere

In a particularly preferred embodiment, the target protein complex is a biochemically functional sarcomere preparation. The functional biochemical behavior of the sarcomere, including calcium sensitivity of ATPase hydrolysis, may be reconstituted from purified individual components. Since all the regulatory components are present, this system allows for simultaneous screening of the entire protein machinery at once.

A particularly preferred target protein complex is a biochemically functional sarcomere comprising myosin, actin, tropomyosin, and the troponin complex. As such, preferred target proteins include, but are not limited to, cytoskeletal proteins including, but not limited to, myosins, actins, tropomyosins, and troponins. Suitable target proteins also include fragments of these proteins. In a preferred embodiment, the target proteins are from mammalian cells.

More specifically, using standard purification techniques (Margossian S S and Lowey S. (1982) Methods Enzymol 85:55–71), adapted to yield larger quantities of protein, gram quantities of myosin, actin, and the regulatory proteins were obtained. The myosin is treated with chymotrypsin to generate the S1 fragment; as opposed to intact myosin, S1 is a soluble protein at salt concentrations necessary for ATPase determination. These proteins can be combined in the proper ratios to reconstitute calcium regulated myosin ATPase activity with ATPase activation ratios of between about 5 and 20 fold and more preferably of up to about 10 fold. This highly regulated sarcomere can be prepared in reliably in large quantities and used for high throughput screening as described below.

III. High Throughput Screening

In a preferred embodiment, activity is measured by the methods disclosed in Ser. No. 09/314,464, filed May 18, 1999, U.S Pat. No. 6,410,254 which is incorporated herein by reference in its entirety. These methods are preferably used in multiwell plate formats and are ideally suited for high throughput screening systems to identify lead compounds for medical therapeutic use and can also be used for diagnostics. More specifically, ADP or phosphate is used as the readout for protein activity.

The ADP or phosphate level can be monitored using coupling enzyme systems to result in changes in the absorbance or fluorescence of the assay mixture relative to a control mixture to determine if the test compound or mixture of test compounds has an affect on the protein function. This may be done with a single measurement but is preferably done with multiple measurements of the same sample at different times. In the case of multiple measurements, the absolute rate of the protein activity can be determined, and such measurements have higher specificity particularly in the presence of test compounds that have similar absorbance or fluorescence properties to that of the enzymatic readout.

In a preferred embodiment, the target protein complex comprises a biochemically functional sarcomere. Compounds which modulate the activity of the complex or one or more of the proteins thereof can be found by monitoring the production of either ADP or phosphate by a variety of methods.

There are several mechanisms by which candidate agents might modulate the target protein complex. One might increase the rate at which myosin hydrolyzes ATP. Since, ATP hydrolysis is coupled to force production, this increase would be expected to increase the force of muscle contraction. In the presence of actin, myosin ATPase activity is stimulated>100 fold. Thus, ATP hydrolysis not only measures myosin enzymatic activity but also its interaction with the actin filament. Thus, a compound that modulates the function of the target protein complex is identified by an increase or decrease in the rate of ATP hydrolysis compared to a control assay in the absence of that compound. Preferred compounds will not activate force production or ATPase activity in the absence of calcium.

Alternatively, the force-pCa$^{2+}$ relationship can be altered through the interaction of the candidate agents with the regulatory complex.

In the case of the fully regulated sarcomere, the assay may be performed at any calcium concentration but preferably at calcium concentrations below pCa=4. The calcium concentration chosen can prejudice the assay towards discovering modulators of a specific protein in the complex. For example, at pCa=4 myosin modulators are more likely discovered as the regulatory proteins no longer exert much inhibitory influence over the ATPase at the calcium concentration. Alternatively, in the presence of EGTA (no calcium) compounds that activate the regulatory proteins in a calcium independent fashion may be found. These compounds may then be eliminated from further consideration as preferred compounds will not activate force production or ATPase activity in the absence of calcium. Finally, actin and myosin may be screened in the absence of the regulatory proteins, thus only modulators of the actin-myosin system will be found.

One method for monitoring ADP production is to couple the ADP production to NADH oxidation with the enzymes pyruvate kinase and lactate dehydrogenase and to monitor the NADH level either by absorbance or fluorescence (*Nature* 1956 178:632; *Mol Pharmacol* 1970 Jan;6(1):31–40). One method for monitoring phosphate production is to use purine nucleoside phosphorylase to couple the phosphate production to the cleavage of a purine analog which results in either a change in absorbance (*Proc Natl Acad Sci USA* 1992 Jun. 1;89(11):4884–7) or fluorescence (*Biochem J* 1990 Mar. 1;266(2):611–4). With either method, the rate of ATP hydrolysis by the target protein complex of interest can be measured.

Test compounds can be assayed in a highly parallel fashion by using multiwell plates by placing the compounds either individually in wells or testing them in mixtures. Assay components including the target protein complex, coupling enzymes and substrates, and ATP can then be added to the wells and the absorbance or fluorescence of each well of the plate can be measured with a plate reader.

In a preferred embodiment, the method uses a 384 well plate format and a 25 $\mu$L reaction volume. A pyruvate kinase/lactate dehydrogenase coupled enzyme system (Huang TG and Hackney D D. (1994) J Biol Chem 269(23):16493–501, which is incorporated herein by reference) is used to measure the rate of ATP hydrolysis in each well. As will be appreciated by those in the art, the assay components are added in buffers and reagents. Since the methods outlined herein allow kinetic measurements, the incubation periods are optimized to give adequate detection signals over the background. The assay is done in real time giving the kinetics of ATP hydrolysis which increases the signal to noise ratio of the assay.

IV. Compounds Suitable for Screening

Candidate agents encompass numerous chemical classes, though typically they are organic molecules, preferably small organic molecules having a molecular weight of more than 100 and less than about 2,500 daltons. Candidate agents are obtained from a wide variety of sources including libraries of synthetic or natural compounds. They include peptides, macromolecules, small molecules, chemical and/or biological mixtures, and fungal, bacterial, or algal extracts. Such compounds, or molecules, may be either biological, synthetic organic, or even inorganic compounds, and may be obtained from several sources, including pharmaceutical companies and specialty suppliers of libraries (e.g., combinatorial libraries) of compounds.

Methods of the present invention are well suited for screening libraries of compounds in multiwell plates (e.g., 96-well plates), with a different test compound in each well. In particular, the methods may be employed with combinatorial libraries. A variety of combinatorial libraries of random-sequence oligonucleotides, polypeptides, or synthetic oligomers have been proposed. A number of small-molecule libraries have also been developed.

Combinatorial libraries may be formed by a variety of solution-phase or solid-phase methods in which mixtures of different subunits are added stepwise to growing oligomers or parent compounds, until a desired compound is synthesized. A library of increasing complexity can be formed in this manner, for example, by pooling multiple choices of reagents with each additional subunit step.

The identity of library compounds with desired effects on the target protein complex can be determined by conventional means, such as iterative synthesis methods in which sublibraries containing known residues in one subunit position only are identified as containing active compounds.

Figure 2:
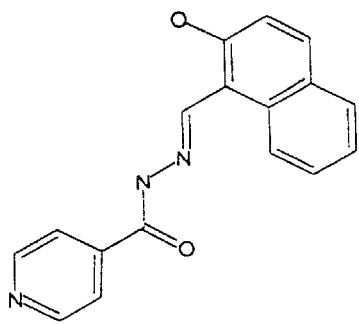
FIG. 2. The top left panel and bottom left panel show the shift to the left and upward of the calcium sensitivity curves for two compounds assayed against a reconstituted sarcomere. The ATPase rate is significantly increased at calcium levels greater than pCa=7. The curves are normalized to the ATPase rate at pCa=4 in control. The top right panel demonstrates that Compound 1 activates cardiac but not skeletal myosin. The bottom right panel shows the lack of effect of Compound 2 when there are no regulatory complex proteins present suggesting the target of this compound is the regulatory complex.
Figure 2:
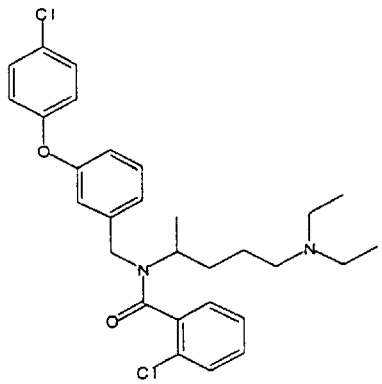
Figure 2:
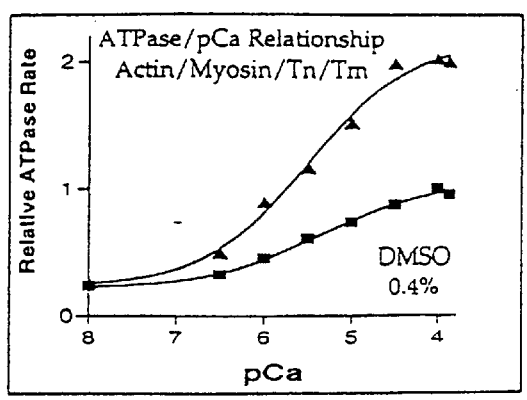
Figure 2:
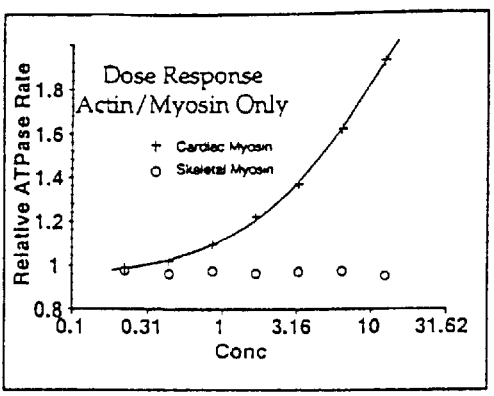
Figure 2:
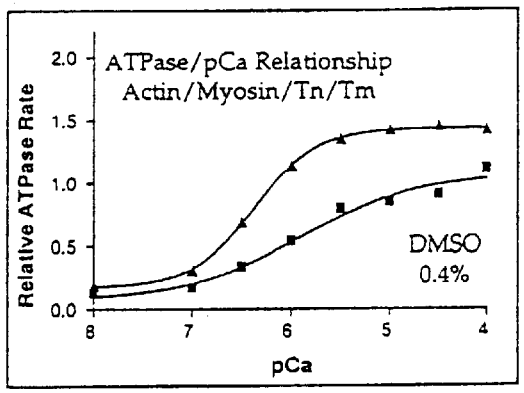
Figure 2:
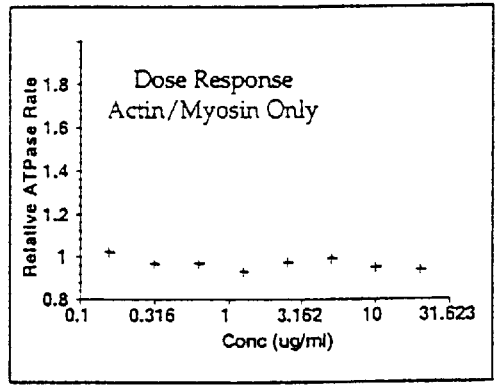

A screen of 20,000 compounds against the reconstituted sarcomere was performed at a pCa of 6.5, a calcium concentration reflective of what is normally reached in vivo during each cardiac cycle. Six compounds were identified that increased the sarcomere ATPase rate by 40% over control or greater at a compound concentration of 10 $\mu$M. Three of the activators were myosin activators and were specific for cardiac myosin and did not appreciably activate skeletal myosin. The other three act on the regulatory apparatus as determined by assaying the compounds against actin and myosin in the absence of the regulatory proteins. (FIG. 2).

While these compounds certainly alter the rate of ATP hydrolysis in a biochemical system, it was then determined whether these compounds would increase the contractile force in a cardiac muscle fiber. The muscle fiber is a densely packed highly ordered actin-myosin structure that is likely to act differently than a soluble biochemical system. These properties were investigated by measuring contractile force in detergent permeabilized cardiac fibers, also known as skinned cardiac fibers. These cardiac fibers retain their intrinsic sarcomeric organization but all aspects of cellular calcium cycling no longer exist. They have two advantages. First, the cellular membrane is not a barrier to compound penetration. Second, any increase in contractile force is related to the compound's direct effect on the sarcomeric proteins rather than an alteration in intracellular calcium levels since calcium concentration is controlled. In addition, they have been used in the past to investigate the properties of this class of agents (Haikala H, Nissinen E, Etemadzadeh E, Levijoki J, Linden I B. (1995) J Cardiovasc Pharmacol 25(5):794–801 and Edes supra). Their disadvantage, however, is that these measurements are time consuming and have to be done carefully in an internally controlled manner since the fibers can be variable.

Figure 3:
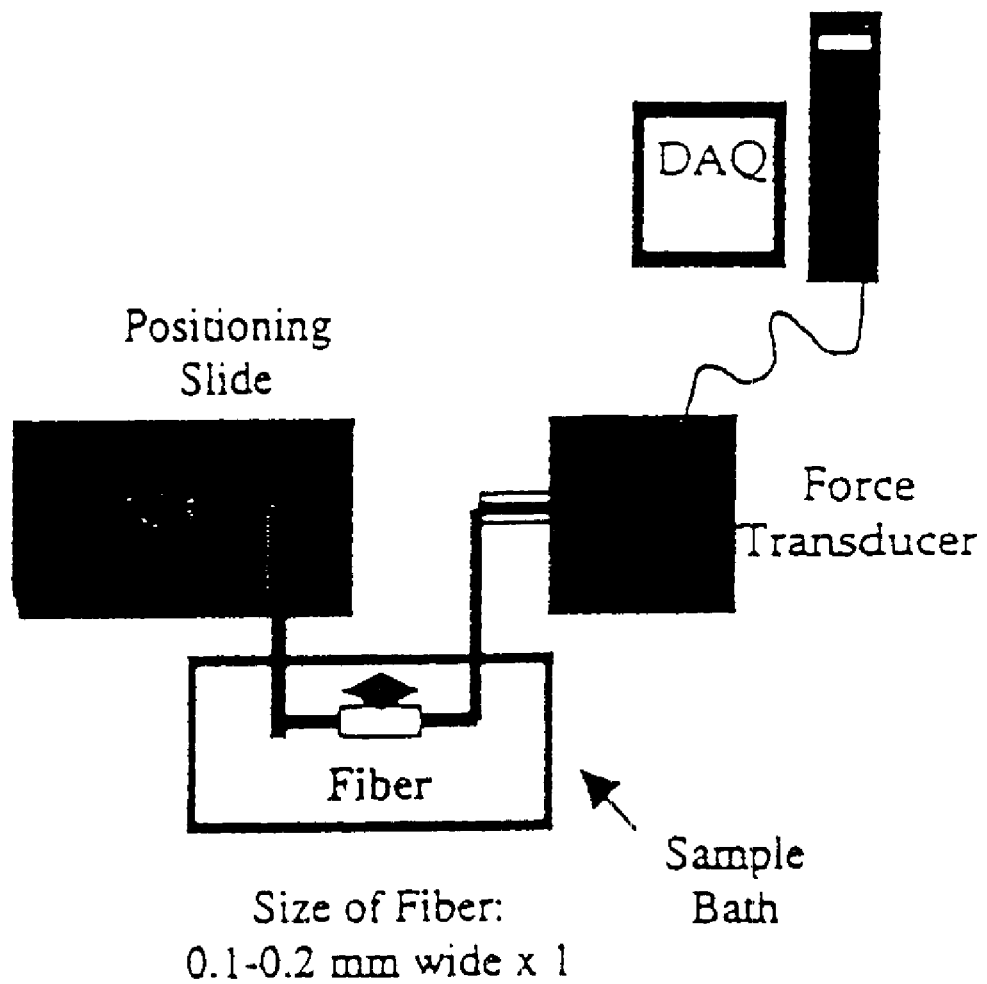
FIG. 3. Diagrammatic representation of the isometric muscle fiber apparatus. Major individual components and their sources are: Force Transducer, 400A Force Transducer (Aurora Scientific, Ontario, Canada); Data Acquisition, PCI-MIO-16E-4 16 channel A/D Board, 250 Khz, 12 bit (National Instruments, Dallas, Tex.); Software, Labview Development System (National Instruments, Dallas, Tex.); Vibration Isolation, VH Isolation Workstation) Newport Corp, Irvine, Calif.); Microscope, Zeiss Stemi 2000-C Dissecting Microscope. Fiber Preparation is as follows: Pig hearts are removed from freshly slaughtered pigs (~1hr) and transported on ice. Trabeculae are dissected from the right ventricle, and placed in ice cold High Relaxing (HR) solution containing 36 mM K-MOPS, 53.4 mM KCl, 7 mM MgCl2, 25 uM CaCl2, 10 mM EGTA, 10.6 mM creatine phosphate, 5.4 mM ATP, 1 mM DTT, and 0.03 mg/ml creatine kinase (pH 7.0). Thin bundles of muscle fibers (1–2 mm in diameter) are dissected from the trabeculae in HR solution, and the fibers are extracted overnight (12–16 hours) at 4° C. in HR solution containing 1% Triton X-100 and a protease inhibitor cocktail. Fibers are then transferred to a 1:1 mixture of HR solution and glycerol, also containing protease inhibitors, and stored at −20° C.

Tension measurements of muscle fibers are made by mounting the muscle fiber at one end to a stationary post and mounting the other end to a transducer that can measure force (FIG. 3). After stretching the fiber to remove slack, the force transducer records increased tension as the fiber begins to contract. This measurement is called the isometric tension, since the fiber is not allowed to shorten. Activation of the permeabilized muscle fiber is accomplished by placing it in a buffered calcium solution.

The contractile properties of the cardiac specific myosin activator Compound 1 (FIG. 3) in skinned cardiac fibers have been determined. This compound exhibited very little augmentation of force at low calcium or in the absence of calcium (the EGTA data point) and reasonable potency.

V. Additional Applications

In addition, the technology platform and secondary assays developed through this project would be useful for discovering agents to treat the large population with diastolic heart failure where the primary contractile defect is in relaxation (Braunwald E. (1997) *Heart Disease: A textbook of cardiovascular medicine*. W. B. Saunders, Philadelphia. Chapters 12, 16, and 17). A second myosin motor, smooth muscle myosin, is also an attractive target protein complex. In this case, finding potent modulators of the motor would find uses in treating conditions where smooth muscle contraction is part of the pathophysiological process. These disease areas include asthma, glaucoma, hypertension, and pre-term uterine labor.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety.

EXPERIMENTAL

Example 1

First, sufficient amounts of sarcomeric proteins from bovine heart were purified. Standard methods of isolation were utilized and the final products shown in FIG. 1. Myosin is purified by successive rounds of solubilization and pre-cipitation in high and low salt buffers. The concentration was determined using an extinction coefficient ~0.53 $cm^2$/mg. The myosin was then cut with chymotrypsin in the presence of EDTA to generate the S1 fragment which is soluble at the low salt conditions optimal for ATPase activity (Margossian supra).

Actin was purified by first preparing an ether powder of cardiac muscle (Zot HG and Potter J D. (1981) Preparative Biochemistry 11:381–395) as described below. Subsequently, actin was cycled between the filamentous and soluble state through rounds of centrifugation and dialysis (Spudich J A and Watt S. (1971) J. Biol. Chem. 246:4866–4871). It was stored in the filamentous state at 4° C.

Tropomyosin was extracted from the ether powder and separated from the other proteins based on pH dependent precipitations followed by successive ammonium sulfate cuts at 53% and 65% (Smillie LB. (1981) Methods Enzymol 85 Pt B:234–41). The troponins were isolated as an intact complex of TnC, TnT, and TnI. Ether powder is extracted in a high salt buffer. Successive ammonium sulfate cuts of 30% and 45% were done; the precipitate was solubilized by dialysis into a low salt buffer and then further purified on a DEAE Toyopearl column with a 25–350 mM KCl gradient. There was no measurable ATPase in any of the components except for myosin which naturally had a very low basal ATPase in the absence of actin.

Just prior to screening, the actin, tropomyosin and tropo-nin complex were mixed together in the proper ratio (7:1:1) to achieve maximal calcium regulation of the actin filament (FIG. 1). The screen was conducted at a pCa=6.5. This calcium concentration is in the physiological range during muscle contraction and is above the inflection point on the pCa curve (FIG. 1). Thus, the steep slope of the curve at this point will magnify the effect of ATPase activators that shift calcium sensitivity to the left.

To measure the generation of ADP during the reaction, a pyruvate kinase/lactate dehydrogenase/NADH coupled enzyme system (PK/LDH) was added to the actin. The myosin was kept separately. The plates are read in real time so that kinetic curves are obtained.

These compounds were in DMSO and were already spotted onto the bottoms of 384 well plates at 10 to 40 $\mu$g/ml final concentration.

Target class was then determined. Actin and myosin (in this case the S1 fragment) were mixed with ATP, compound at 10 $\mu$M and the PK/LDH coupled enzyme system (FIG. 1). The ATPase rate in the presence of compound was compared to control (an equivalent amount of DMSO). Hits that can activate the myosin ATPase in the absence of the regulatory proteins exert their effects against either actin or myosin (an example is shown in FIG. 1).

For myosin activators, selectivity for cardiac myosin versus skeletal myosin was determined by substituting the cardiac myosin with skeletal myosin. Rabbit cardiac and skeletal myosins were be used to avoid any effect of testing proteins from different species. Since the compounds were identified against bovine myosin, this test also demonstrates whether the compounds are isoform specific but not species specific. Finally, since cardiac actin was used in all assays, compounds that activate cardiac myosin but not skeletal myosin will formally be identified as interacting with myosin rather than actin.

By elimination, hits that don't activate in the absence of the regulatory complex but do activate in the presence of the regulatory complex interact with this set of proteins to produce their effect. Specificity again will be tested by substituting homologous skeletal regulatory proteins for their cardiac counterparts. In the case of the troponins, it will be possible eventually to demonstrate activity against the human targets as these are the only sarcomeric proteins that can be expressed easily in bacteria.

Each class of activators could have detrimental properties that can be determined by ATPase assay. The myosin hits could turn on the myosin ATPase in the absence of actin, uncoupling the actin-myosin activated ATPase. This basal ATPase is easy to ascertain by measuring myosin ATPase in the absence of actin. The regulatory hit compounds could relieve regulatory inhibition of myosin ATPase in the absence of calcium. ATPase assays of the regulatory activators in the presence of EGTA will rule out calcium independent activation. These tests will be performed as part of compound characterization.

All tension measurements are made using the following general protocol. Skinned fibers are further dissected from muscle bundles before use to ~0.3–0.6 mm diameter and approximately 0.5–1 cm in length. These fibers are mounted between the manual positioner and tension transducer using cellulose acetate dissolved in acetone. Tension measurements are made at 20–22° C., using buffers similar to HR solution, except for the substitution of 0.1 mM EGTA and various amounts of $CaCl_2$ to give pCa values between 8 and 4. All solutions contain 5 mM K-phosphate (pH 7.0) to reduce maximal tension development and prolong fiber life and reproducibility. Fibers are stretched until tension begins to increase measurably, and then cycled several times between relaxing (0.1 mM EGTA) and pCa 4.0 to measure maximal tension development and ensure fiber integrity. Baseline tension is subtracted from all measurements, and the subsequent values are normalized to the maximal tension produced at pCa 4.0 (100%). Measurements are made at various calcium concentrations (calculated using the program MAXChelator, http://www.stanford.edul~cpatton/maxc.html, that adjusts for the presence of ATP and magnesium) in the presence and absence of compound.

Example 2

Actin Preparation

1. Extract powder (as prepared in Example 3 or 4 below) with 20 ml buffer A (see below, add BME and ATP just prior to use in each of the following steps) per gram of powder (200 ml per 10 g). Use a large 4L beaker for 150 g of powder. Mix vigorously to dissolve powder. Stir at 4° C. for 30 min.
2. Separate extract from the hydrated powder by squeezing through several layers of cheesecloth. Cheesecloth should be pre-sterilized by microwaving damp for 1–2 min.
3. Re-extract the residue with the same volume of buffer A and combine extracts.
4. Spin in JLA10 rotor(s) for 1 hr. at 10K rpm (4° C.). Collect supernatant through 2 layers of cheesecloth.
5. Add ATP to 0.2 mM and $MgCl_2$ to 50 mM. Stir on stir plate at 4° C. for 60 minutes to allow actin to polymerize/form para-crystals.
6. Slowly add solid KCl to 0.6 M (45 g/l). Stir at 4C for 30 min.
7. Spin in JLA10rotor(s) at 10K rpm for 1 hr.
8. Depolymerization: Quickly rinse surface of pellets with buffer A and dispose of wash. Soften the pellets by pre-incubation on ice with small amount of buffer A in each tube (use less than half of final resuspension volume total in all tubes). Resuspend by hand first with cell scraper and combine pellets. Wash tubes with extra buffer using a 25 ml pipette and motorized pipettor, aggressively removing actin from sides of tubes. Homogenize in large dounce in cold buffer A on ice. Use 3 ml per gram of powder originally extracted.
9. Dialyze against buffer A with 4 changes over 48 hour period.
10. Collect dialyzed actin and spin in the 45Ti rotor at 40 Krpm for 1.5 hr. (4° C.).
11. Collect supernatant (G-Actin). Save a sample for gel analysis and determination of protein concentration.

To polymerize G-actin for storage add KCl to 50 mM (from 3 M stock), $MaCl_2$ to 1 mM, and $NaN_3$ to 0.02% (from 10% stock). Store at 4° C. Do not freeze.
Buffer A: 2 mM tris/HCl, 0.2 mM $CaCl_2$, 0.5 mM (36 ul/L) 2-mercaptoethanol, 0.2 mM $Na_2ATP$ (added fresh), and 0.005% Na-azide; pH 8.0.

Example 3

Powder Preparation

1. Volumes are given per ~1000 g of the minced muscle.
2. Pre-cut and boil cheesecloth for. 10 min. in water. Drain and dry.
3. Mince chicken breast in a prechilled meat grinder.
4. Extract with stirring in 2 L of 0.1 M KCl, 0.15 M K-phosphate, pH 6.5 for 10 min at 4° C. Spin 5000 rpm, 10 min, 4° C. in JLA. Collect the pellet.
5. Extract pellets with stirring with 2 L of 0.05 M $NaHCO_3$ for 5 min. Spin 5000 rpm, 10min, 4C in JLA. Collect the pellet. Repeat the extraction once more.
6. Extract the filtered residue with 2 L of 1 mM EDTA, pH 7.0 for 10 min with stirring.
7. Extract with 2 L of $H_{20}$ for 5 min with stirring. Spin 10000 rpm, 15min, 4C in JLA. Carefully collect the pellet, part of which will be loose and gelatinous.
8. Extract 5 times with acetone (2 L of acetone for 10 min each with stirring). Squeeze through cheese-cloth gently. All acetone extractions are performed at room temperature. Acetone should be prechilled to 4° C.
9. Drying: Place the filtered residue spread on a cheese-cloth in a large glass tray and leave in a hood overnight. When the residue is dry, put in a wide mouth plastic bottle and store at 20° C.

Example 4

Alternate Powder Preparation

Based on Zot & Potter (1981) Prep. Biochem. 11(4) pp.381–395.

1. Dissect left ventricles of the cardiac muscle. Remove as much of the pericardial tissue and fat as possible. Grind in a prechilled meat grinder. Weigh.
2. Prepare 5 volumes of Extract buffer. Be sure the pH=8.0. Then, homogenize the meat in a blender, 4×15secs on blend with 15 secs in between. Do this with 1 volume (weight/volume) of buffer taken from the 5 volumes already prepared. Add the homogenate back to the extract buffer and stir until well mixed (5 minutes).
3. Filter through one layer of cheese cloth in large polypropylene strainer. Resuspend back into 5 volumes of extract buffer as above.
4. Repeat step 3) 4 more times. At the end, do not resuspend in extraction buffer but proceed to step 5). The pellets should be yellow white.
5. Resuspend in 3 volumes (according to original weight) of 95% cold Ethanol. Stir for 5 min and squeeze through cheesecloth as above, repeat two more times.
6. Weigh squeezed residue and then resuspend in 3 volumes (new weight/volume) of cold diethyl ether.
7. Repeat step 6) a total of 3 times.
8. Leave overnight in a single layer on a cheese cloth in a glass tray.
9. When dry, collect the powder, weigh and store in a wide-mouth jar at 4° C.

EXTRACT BUFFER: 50 mM KCl, 5 mM Tris pH 8.0
Prepare as 50× concentrate:

|  |  | For 2L |
| --- | --- | --- |
| 250 mM Tris pH 8.0. Tris Base pH to 8.0 with conc. HCl, then add: | 121.14 g/mol | 60.6 g |
| 2.5 M KCl | 74.55 g/mol | 372 g |

What is claimed is:
1. A method of identifying a candidate agent as a modulator of function of a target protein complex wherein said target protein complex comprises a biochemically functional sarcomere and said method comprises:
   a) adding in vitro a candidate agent to a mixture comprising a target protein complex that directly or indirectly produces ADP or phosphate under conditions which normally allow the production of ADP or phosphate, wherein said target protein complex comprises isolated myosin and isolated actin;

b) subjecting the mixture to an enzymatic reaction that uses said ADP or phosphate as a substrate under conditions which normally allow the ADP or phosphate to be utilized; and determining the level of activity of the enzymatic reaction wherein a change in said level between the presence and absence of said candidate agent indicates that said candidate agent is a modulator of said target protein function.

2. The method of claim 1, wherein said determining occurs by a fluorescent, luminescent, radioactive, or absorbance readout.

3. The method of claim 1, wherein said level of activity of said enzymatic reaction is determined at multiple time points.

4. The method of claim 1, wherein a plurality of candidate agents are added.

5. The method of claim 1, wherein said target protein complex directly produces phosphate or ADP.

6. The method of claim 1, wherein said target protein complex comprises a mixture of myosin, actin, and cardiac regulatory proteins.

7. The method of claim 6, wherein said candidate agent activates myosin.

8. The method of claim 6, wherein said candidate agent modulates a cardiac regulatory protein.

9. The method of claim 1, wherein the enzymatic reaction occurs at a calcium concentration below pCa equal to 4.

10. The method of claim 1, wherein the enzymatic reaction occurs at a calcium concentration of about pCa equal to 4.

11. The method of claim 1, wherein the enzymatic reaction occurs at a calcium concentration of about pCa equal to 6.5.

12. The method of claim 1, wherein the enzymatic reaction occurs in the presence of ethylenebis(oxyethylenenitrilo)tetraacetic acid (EGTA).

* * * * *